(12) United States Patent
Kimura et al.

(10) Patent No.: US 9,386,935 B2
(45) Date of Patent: Jul. 12, 2016

(54) ELECTROCARDIOGRAM ANALYZER

(71) Applicant: NIHON KOHDEN CORPORATION, Tokyo (JP)

(72) Inventors: Kei Kimura, Tokyo (JP); Kazuhiro Sekikawa, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/166,169

(22) Filed: Jan. 28, 2014

(65) Prior Publication Data

US 2014/0221860 A1 Aug. 7, 2014

(30) Foreign Application Priority Data

Feb. 5, 2013 (JP) ................. 2013-020433

(51) Int. Cl.
*A61B 5/04* (2006.01)
*A61B 5/0452* (2006.01)
*A61B 5/0432* (2006.01)

(52) U.S. Cl.
CPC ........... *A61B 5/0452* (2013.01); *A61B 5/04525* (2013.01); *A61B 5/0432* (2013.01)

(58) Field of Classification Search
USPC ........................................................ 600/515
See application file for complete search history.

(56) References Cited

U.S. PATENT DOCUMENTS

| | | | |
|---|---|---|---|
| 4,336,810 A | 6/1982 | Anderson et al. | |
| 2004/0127805 A1 | 7/2004 | MacAdam et al. | |
| 2004/0215090 A1 | 10/2004 | Erkkila et al. | |
| 2004/0260192 A1 | 12/2004 | Yamamoto | |
| 2006/0116725 A1 | 6/2006 | Palreddy et al. | |
| 2009/0125075 A1 | 5/2009 | Palreddy et al. | |
| 2010/0152598 A1* | 6/2010 | Zhang ........................... 600/515 | |
| 2012/0184858 A1 | 7/2012 | Harlev et al. | |

FOREIGN PATENT DOCUMENTS

| | | |
|---|---|---|
| CN | 1572238 A | 2/2005 |
| CN | 101102812 A | 1/2008 |
| CN | 102697492 A | 10/2012 |

(Continued)

OTHER PUBLICATIONS

Office Action dated Mar. 24, 2014, issued by the European Patent Office in counterpart European Application No. 14152962.8.
Notification of First Office Action issued on Mar. 21, 2016 by the State Intellectual Property Office of PR China in related Application No. 201410042151.3.

(Continued)

*Primary Examiner* — Nicole F Lavert
(74) *Attorney, Agent, or Firm* — Sughrue Mion, PLLC

(57) ABSTRACT

An electrocardiogram analyzer has a measurement section for measuring an electrocardiographic signal; a determination unit for determining, from arrhythmia determination reference information that is information pertinent to arrhythmia, whether or not an electrocardiogram multiplex, which includes a first predetermined number of heart beats, in the thus-measured electrocardiographic signal is arrhythmia; a reference waveform determination unit that determines a reference waveform from the electrocardiogram complex including the first predetermined number of heart beats when the determination unit has determined that the electrocardiogram complex is not arrhythmia, storing the thus determined reference waveform; and an analysis unit that performs an analysis as to whether or not an electrocardiogram complex being measured is arrhythmia by use of the stored reference waveform.

5 Claims, 6 Drawing Sheets

(56) References Cited

FOREIGN PATENT DOCUMENTS

| EP | 1486165 | A1 | 12/2004 |
|----|---------|----|---------|
| EP | 2540222 | A2 | 1/2013 |
| JP | 2834057 | B2 | 10/1998 |

OTHER PUBLICATIONS

Communication from the European Patent Office issued May 10, 2016 in corresponding European Patent Application No. 14 152 962.8.

* cited by examiner

ELECTROCARDIOGRAM ANALYZER

BACKGROUND

The presently disclosed subject matter relates to an electrocardiogram analyzer for analyzing an electrocardiographic signal acquired from a living body and also analyzing cardiac activities by monitoring arrhythmia, or the like.

Throughout the specification, monitoring arrhythmia or monitoring includes comparing an electrocardiographic complex of a test subject acquired per heart beat with a reference waveform, to thus determine if the heart beat is arrhythmia, and an alarm is generated to call attention when the heart beat is determined to be arrhythmia. A plurality of types of alarms are sometimes generated in accordance with a degree of arrhythmia.

An apparatus of this type hitherto stores a reference waveform previously determined through electrocardiogram complex learning, and arrhythmia is monitored by reference to the reference waveform. Here, electrocardiogram complex learning is usually practiced at the start of measurement when the test subject first experiences electrocardiogram measurement. An electrocardiogram appropriate for the test subject is not always determined to be a reference waveform. Specifically, a waveform of arrhythmia, which deviates from a normal electrocardiographic complex of the test subject, could be determined as a reference waveform.

Provided that electrocardiogram complex learning is performed in the middle of occurrence of arrhythmia, a waveform of the arrhythmia will be determined as a reference waveform. A fact that arrhythmia has occurred during the learning is overlooked. In addition, there occurs a problem of appropriate analysis being not performed during arrhythmia monitoring subsequent to electrocardiogram complex learning.

On the contrary, there is a known electrocardiogram analyzer that automatically chooses multiple representative heart beats from among a plurality of heart beats in one analysis operation and that analyzes the thus-selected plural representative heart beats, displaying names of diagnoses with regard to the respective heart beats (see Japanese Patent No. 2834057).

The apparatus is advantageous in that an appropriate name of a diagnosis is displayed with regard to a heart beat, which does not include any artifact, in the plurality of representative heart beats. However, there is a necessity of identifying the diagnosis. For this reason, the apparatus is inappropriate for a case where there is a desire for acquiring an appropriate result from the apparatus, and the apparatus also raises a problem of time being consumed when a user makes a determination.

SUMMARY

This presently disclosed subject matter provides an electrocardiogram analyzer capable of preventing a problem of a waveform of arrhythmia being determined as a reference waveform. Further, the presently disclosed subject matter aims at providing an electrocardiogram analyzer that does not overlook arrhythmia even during the beginning of learning.

It is therefore an aspect of the presently disclosed subject matter to provide an electrocardiogram analyzer comprising: a measurement section configured to measure an electrocardiographic signal; a determination unit configured to determine, from arrhythmia determination reference information that is pertinent to arrhythmia, whether or not an electrocardiogram complex, which includes a first predetermined number of heart beats, in the thus-measured electrocardiographic signal indicates arrhythmia; a reference waveform determination unit configured to determine a reference waveform from the electrocardiogram complex including the first predetermined number of heart beats when the determination unit has determined that the electrocardiogram complex does not indicate arrhythmia, storing the thus determined reference waveform; and an analysis unit configured to perform an analysis as to whether or not an electrocardiogram complex being measured is arrhythmia by use of the stored reference waveform.

The electrocardiogram analyzer may further comprise a selection unit configured to determine reference waveform candidates from an electrocardiogram complex including a second predetermined number of heart beats, which are essentially identical to each other in terms of a contour, in the measured electrocardiographic signal, wherein the electrocardiogram complex including the first predetermined number of heart beats is selected from the reference waveform candidates.

The electrocardiogram analyzer may further comprise an alarm generation unit configured to generate an alarm which represents arrhythmia when the determination unit has determined the electrocardiogram complex as arrhythmia.

The electrocardiogram analyzer may further comprise a reference waveform manual determination unit configured to manually set the reference waveform, wherein, when the reference waveform manual determination unit is actuated, the reference waveform determination unit performs, without regard to a determination rendered by the determination unit, alternate processing including determining the reference waveform from the electrocardiogram complex including the first predetermined number of heart beats and storing the thus-determined reference waveform.

In the electrocardiogram analyzer, when the reference waveform determination unit has performed alternate processing, the analysis unit may perform an analysis as to whether or not an electrocardiogram complex which will be subsequently measured exhibits a feature of a reference waveform stored by the reference waveform determination unit; and processing proceeds to a determination which will be made by the determination unit when an electrocardiogram waveform exhibiting the feature of the reference waveform is not detected for a given period of time.

DETAILED DESCRIPTION OF EMBODIMENTS

Figure 1:
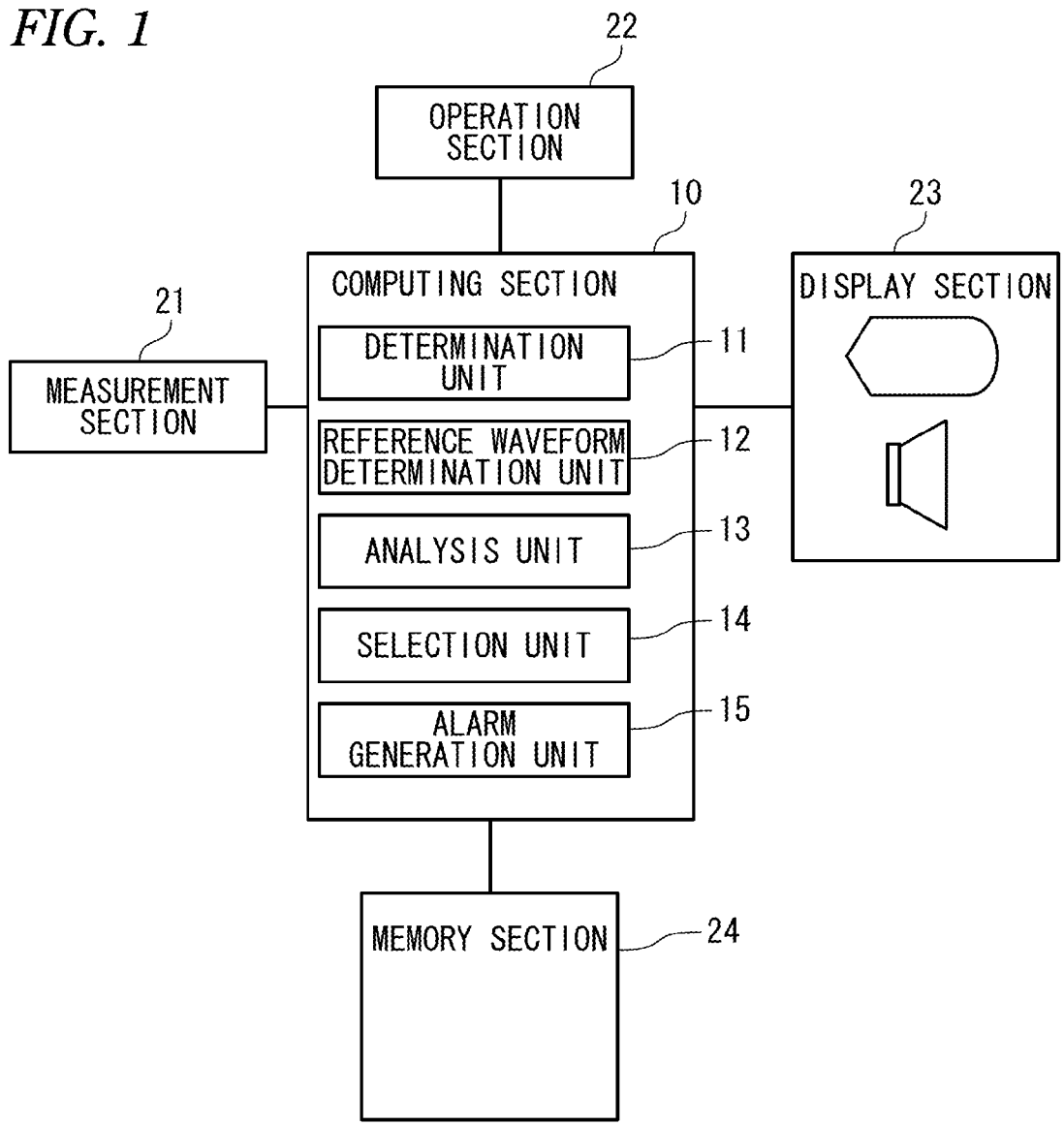
FIG. 1 is a block diagram illustrating an embodiment of an electrocardiogram analyzer of the presently disclosed subject matter.

An electrocardiogram analyzer of the presently disclosed subject matter is hereunder described by reference to the accompanying drawings. Throughout the drawings, like constituent elements are assigned like reference numerals, and their repeated explanations are omitted. FIG. 1 is a block diagram illustrating an embodiment of an electrocardiogram analyzer of the presently disclosed subject matter. The electrocardiogram analyzer has a computing section 10 made up of a computer. The computer includes a CPU and memory.

The computing section 10 is connected to a measurement section 21 that measures an electrocardiographic signal. The measurement section 21 has lead electrodes, an amplifier, an A/D converter, and others. In relation to the number of leads, multi-leads, like 12 leads, are acceptable. However, an electrocardiographic signal obtained by way of a mono-lead is to be measured here.

The computing section 10 is connected to an operation section 22, a display section 23, and a memory section 24. The operation section 22 includes a switch for toggling the electrocardiogram analyzer on or off, a reference waveform determination key (a reference waveform manual determination unit) for forcibly taking a reference waveform candidate to be described later as a reference waveform, and a key for deactivating an alarm. A part or entirety of the operation section 22 can be embodied as a touch panel to be placed on a screen for operating keys displayed on a screen of the display section 23. The display section 23 has a display device made up of liquid crystal, a speaker for generating an alarm sound, and others.

The memory section 24 stores a program for electrocardiographic analysis, data pertinent to an electrocardiogram complex which is necessary for analysis, and arrhythmia determination reference information. Information about a determined reference waveform and a time for measurement or analysis are stored in association with identification information of a test subject.

The computing section 10 comprises a determination unit 11, a reference waveform determination unit 12, an analysis unit 13, a selection unit 14, an alarm generation unit 15, and an unillustrated timer. The determination unit 11 determines, from arrhythmia determination reference information relevant to arrhythmia, whether or not an electrocardiogram complex including a first predetermined number of heart beats in a measured electrocardiographic signal is arrhythmia. When the determination unit 11 has determined that the electrocardiogram complex is not arrhythmia, the reference waveform determination unit 12 determines a reference waveform from the electrocardiogram complex including the first predetermined number of heart beats, storing the reference waveform. The analysis unit 13 performs electrocardiographic analysis as to whether or not an electrocardiogram complex being measured is arrhythmia by use of the thus-stored reference waveform.

The selection unit 14 determines a reference waveform candidate from an electrocardiogram complex including a second predetermined number of heart beats, which are essentially equal to each other in terms of a contour, in the waveform of the measured electrocardiographic signal. In the embodiment, the first predetermined number of heart beats is six beats, and the second predetermined number of heart beats is eight beats; however, the predetermined numbers are not limited to these figures. When the determination unit 11 has determined that the electrocardiogram complex is arrhythmia, the alarm generation unit 15 generates an alarm which represents arrhythmia. An alarm is displayed on the display device of the display section 23, and an alarm sound is generated from the speaker.

If an operator has operated the reference waveform determination key of the operation unit that is the operation section 22 at the moment of generation of the arrhythmia alarm, the reference waveform determination unit 12 performs special processing (alternate processing) involving determining a reference waveform from the electrocardiogram complex including the first predetermined number of heart beats without regard to the determination rendered by the determination unit 11 and storing the thus-determined reference waveform. When the reference waveform determination unit 12 has performed special processing, the analysis unit 13 carries out an analysis as to whether or not an electrocardiogram complex which will be measured later exhibits a feature of the reference waveform stored by the reference waveform determination unit 12. When a waveform that exhibits the feature of the stored reference waveform is not detected for a given period of time, the analysis unit 13 performs control such that processing shifts to determination operation which the determination unit 11 performs.

Figure 2:
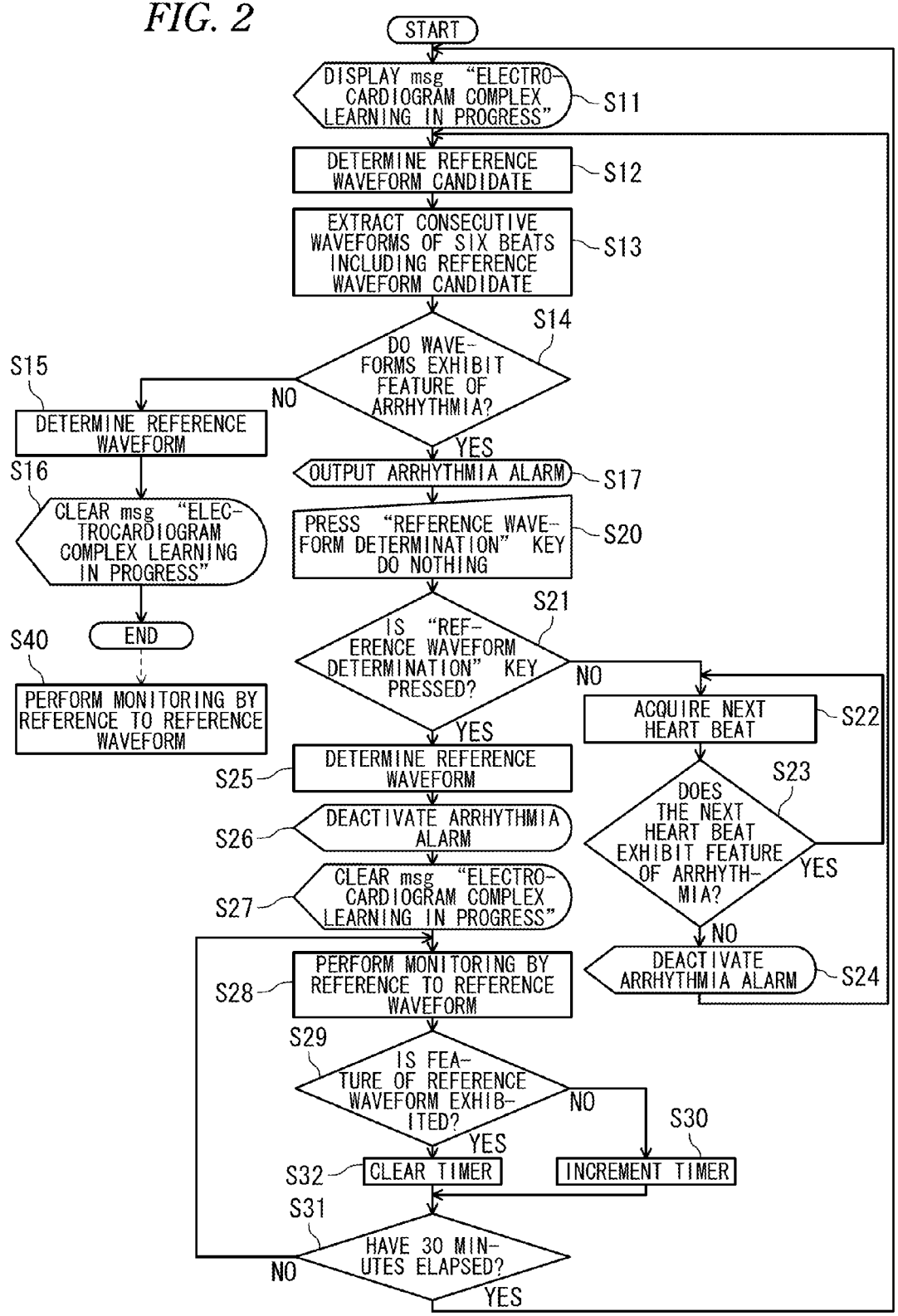
FIG. 2 is a flowchart illustrating operation of the embodiment of the electrocardiogram analyzer of the presently disclosed subject matter.

The electrocardiogram analyzer configured as above loads an electrocardiogram analyzing program corresponding to a flowchart illustrated in FIG. 2 from the memory section 24, executing the program, whereby the electrocardiogram analyzer functions as the aforementioned respective unit and performs operations. The operations are described below by reference to the flowchart illustrated in FIG. 2.

The lead electrodes of the measurement section 21 are attached to predetermined locations on the test subject. The electrocardiogram analyzer is activated by means of the switch of the operation section 22, whereupon measuring an electrocardiogram complex is started according to the program corresponding to the flowchart illustrated in FIG. 2. A message "Electrocardiogram complex learning is in progress" appears on the screen of the display device of the display section 23 under control of the computing section 10, and an electrocardiogram complex being measured is displayed from then on (S11). It is detected that the electrocardiogram complex transmitted from the measurement section 21 includes uniform waveforms of eight beats that are essentially identical with each other in terms of a contour. For instance, a waveform of the eighth beat is determined as a reference waveform candidate (S12 (selection unit 14)).

Waveforms of six beats, which include the reference waveform candidate and which are contiguous from the reference waveform candidate in a timewise direction of retrogression, are extracted (S13). A feature of arrhythmia included in the waveforms is detected (S14 (determination unit 11)). It is herein detected, on the basis of the arrhythmia determination reference information, that the waveforms exhibit a feature of arrhythmia. The arrhythmia determination reference information is reference information, like waveforms of six beats whose QRS waveforms are analogous to each other; waveforms of six beats whose QRS intervals are broad; and waveforms of six beats whose RR spacings are short. Each of the pieces of arrhythmia determination reference information can be determined by means of a threshold value.

Figure 3:
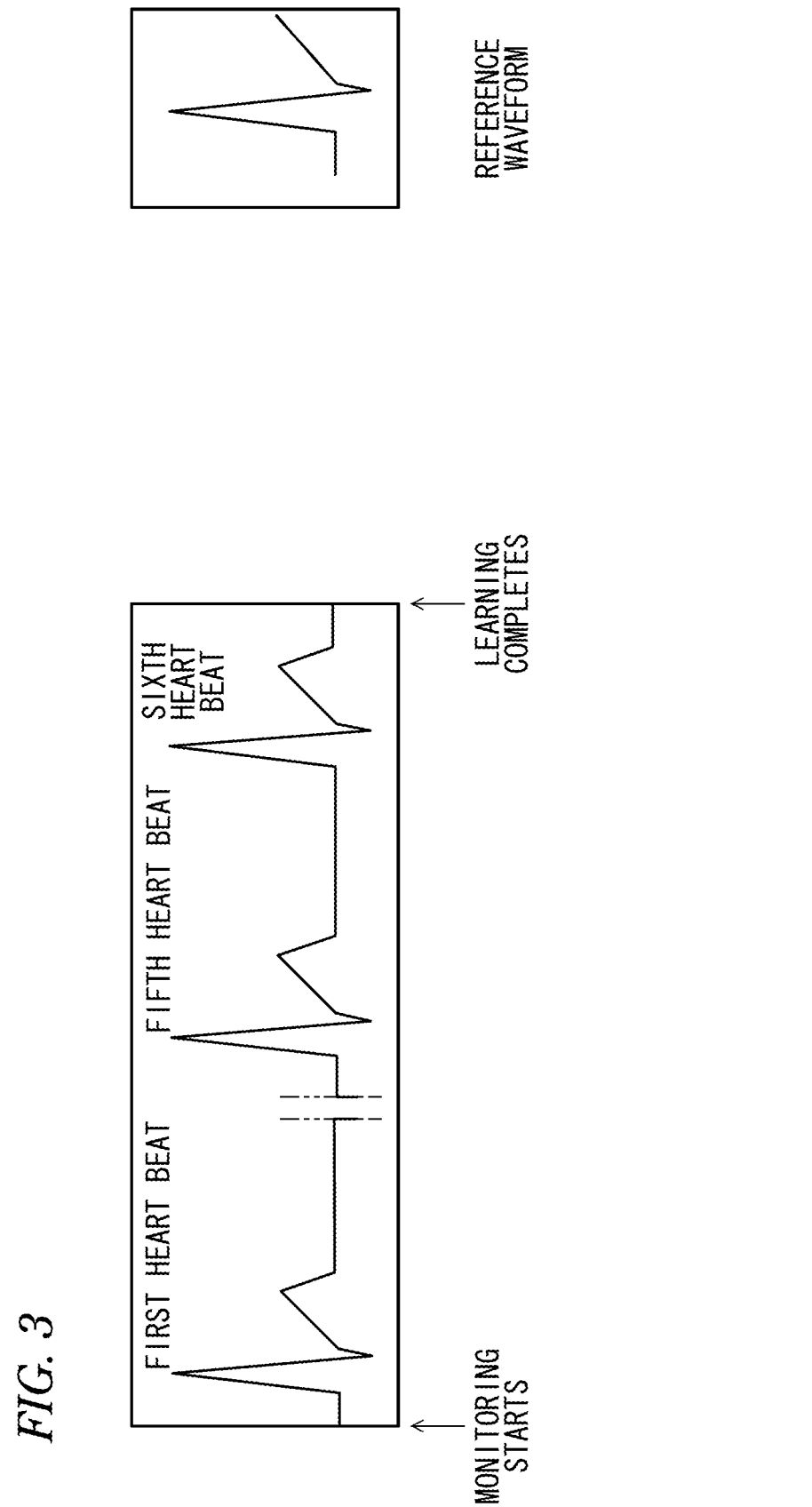
FIG. 3 is a waveform chart illustrating a case where a reference waveform is determined by the embodiment of the electrocardiogram analyzer of the presently disclosed subject matter.

When the waveforms are determined not to exhibit the feature of arrhythmia in step S14 (NO in S14), any one of the waveforms of six beats or a mean waveform is determined as a reference waveform. The thus-determined reference waveform is stored in the memory section 24 along with test subject identification information and time (S15 (reference waveform determination unit 12)). For instance, as illustrated in FIG. 3, when there are uniform waveforms of six beats that do not exhibit the feature of arrhythmia, any one of the waveforms or a mean waveform is stored as a reference waveform.

Further, the message "Electrocardiogram complex learning in progress" displayed on the screen of the display device of the display section 23 under control of the computing section 10 is cleared (S16), whereupon learning processing ends. Monitoring (electrocardiographic analysis) is carried out from this time onward on the basis of the thus-determined reference waveform (S40).

Figure 4:
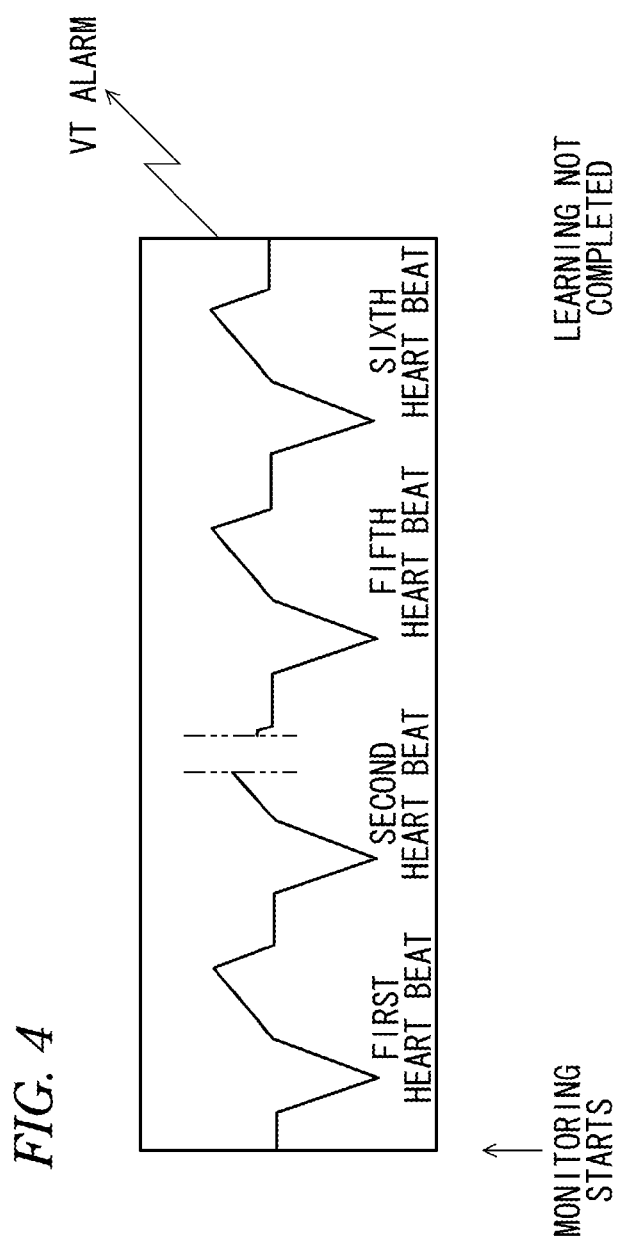
FIG. 4 is a waveform chart illustrating a case where a reference waveform is not determined by the embodiment of the electrocardiogram analyzer of the presently disclosed subject matter.

In the meantime, when the waveforms are determined to exhibit the feature of arrhythmia in step S14 (Yes in S14), an alarm indicating arrhythmia is displayed on the display device of the display section 23, and an alarm indicating arrhythmia is generated from the speaker (S17 (alarm generation unit 15)). FIG. 4 illustrates an example waveform appearing in this case. In the example, since all of the waveforms of six beats exhibit wide QRS intervals, the determination unit 11 determines that the waveforms exhibit the feature of arrhythmia (ventricular tachycardia: VT), generating an alarm (a VT alarm) illustrating ventricular tachycardia. A reference waveform is not yet determined in this stage.

In this state, the operator may set as reference waveforms the waveforms of six beats displayed on the screen of the display device of the display section 23. Although the determination unit 11 has determined that the waveforms of six beats are arrhythmia, the waveforms can be set as reference waveforms at operator's judgment. In order to set the waveforms of six beats as reference waveforms, the "Reference waveform determination key" is actuated (S20).

In step S21, detection is performed as to whether or not the "Reference waveform determination" key is actuated. When the "Reference waveform determination" key is determined not to be actuated in step S21 (No in S21), a subsequent electrocardiograph complex including one heart beat is sampled (S22). Detection is performed as to whether or not retrospectively-consecutive waveforms of six heart beats, including the waveform, exhibit a feature of arrhythmia (S23 (determination unit 11)). When the heart beats are determined to exhibit the feature of arrhythmia in step S23 (Yes in S23), electrocardiogram complex learning is continued by iterating processing pertinent to steps S22 and S23.

Figure 5:
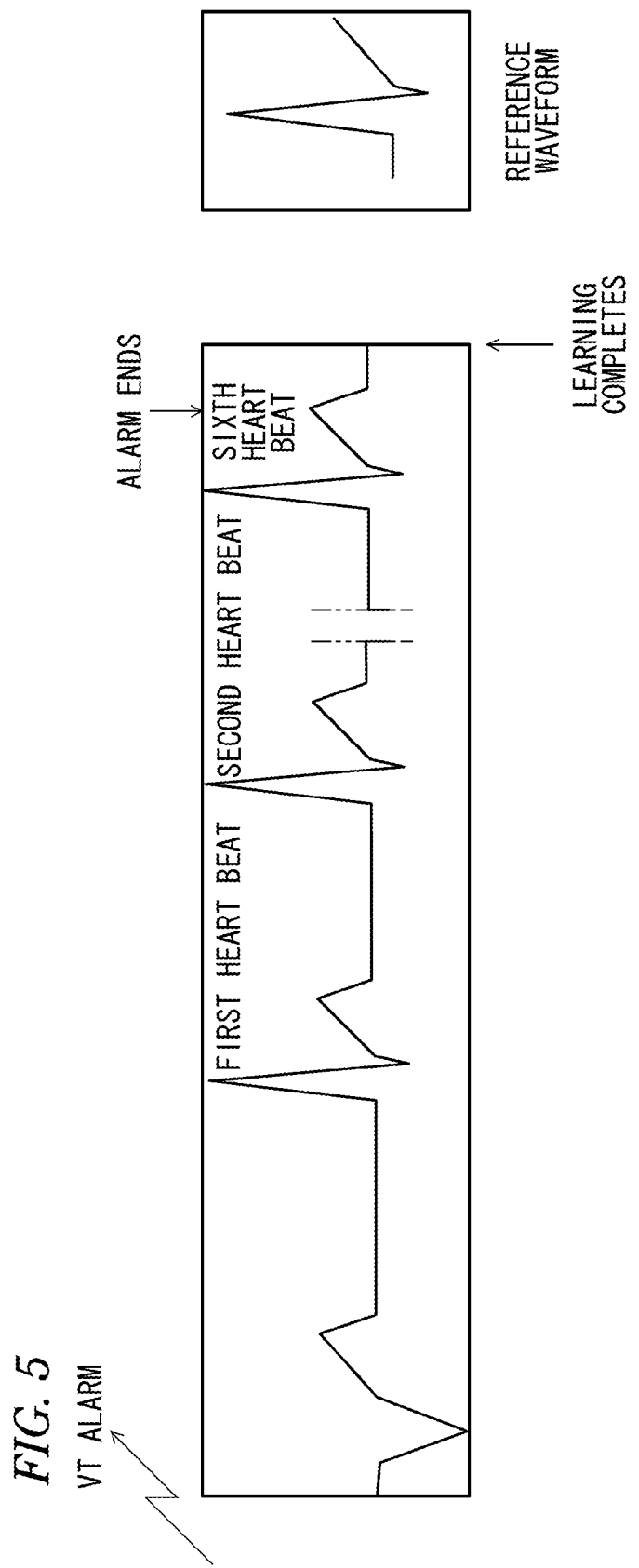
FIG. 5 is a waveform chart illustrating an example in which an arrhythmia alarm is generated at the beginning of learning when the electrocardiogram analyzer of the embodiment of the presently disclosed subject matter determines a reference waveform and where a reference waveform is subsequently determined.

When the heart beats are determined not to exhibit the feature of arrhythmia in step S23 (No in S23), the arrhythmia alarm is deactivated (S24). Processing returns to step S12, where electrocardiogram complex learning is further continued. For instance, the alarm is deactivated when the state in which the waveforms have been determined to be arrhythmia is followed by uniform waveforms that are determined not to exhibit the feature of arrhythmia as illustrated in FIG. 5 (S24). In processing from step S12 onward, a reference waveform is expected to be determined and stored.

Figure 6:
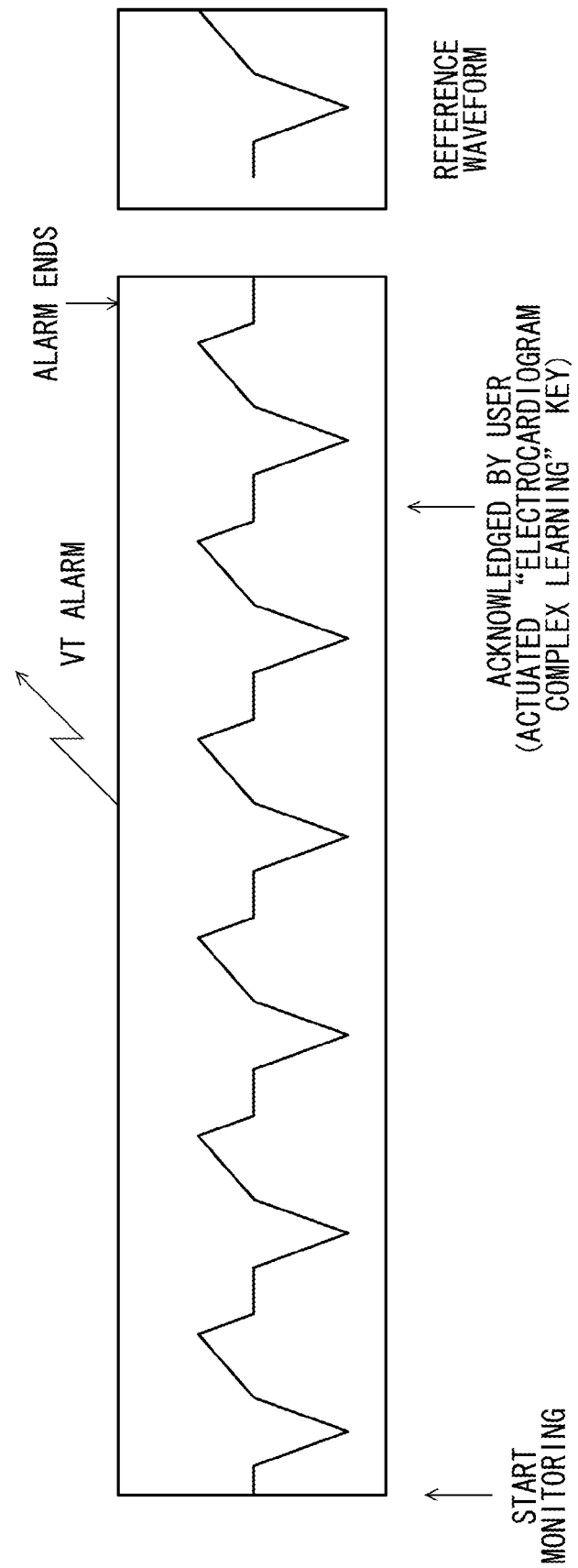
FIG. 6 is a waveform chart illustrating an example in which a user performs acknowledgement when the embodiment of the electrocardiogram analyzer of the presently disclosed subject matter determines a reference waveform and where a reference waveform is determined from the acknowledgment.

When the "Reference waveform determination" key is determined to be actuated in step S21 (Yes in S21), there is performed special processing including determining a reference waveform from consecutive waveforms of six beats appearing at this point in time and storing the thus-determined reference waveform (S25 (reference waveform determination unit)), and the alarm is deactivated (S26). As above, when the alarm is generated, the "Reference waveform determination" key can be actuated in accordance with the judgment of the operator who has visually observed the electrocardiogram complex displayed on the display device of the display section 23, so that the waveform can be acknowledged as the reference waveform. Special processing is thereby performed as illustrated in FIG. 6, and the reference waveform is determined and stored.

Subsequently to step S26, the message "Electrocardiogram complex learning in progress" displayed on the display device of the display section 23 under control of the computing section 10 is cleared (S27). Step S27 is followed by monitoring (analysis of an electrocardiogram complex) that is practiced on the basis of the reference waveform determined in step S25 (S28).

Each time one waveform appears, an analytical determination is made concurrently with monitoring as to whether or not the waveform exhibits the feature of the reference waveform stored during special processing (S29 (analysis unit)). For instance, when a degree of similarity between a waveform of interest and the stored reference waveform is a threshold value or less, the waveform is determined not to exhibit the "feature of the reference waveform" (No in S29). Since the reference waveform employed at this point in time has been determined to be arrhythmia by the determination unit 11 and acknowledged by the operator, the analytical determination is performed because it is impossible to negate a possibility of the waveform which does not exhibit the feature of the reference waveform being a normal waveform.

When the waveform is determined not to exhibit the feature of the reference waveform in step S29, a timer is incremented (is caused to advance) (S30), thereby detecting whether or not 30 minutes, or a predetermined period of time, have elapsed (S31). When 30 minutes have not yet elapsed (No in S31), processing returns to step S28, where processing is continued.

In the meantime, when the waveform is determined to exhibit the feature of the reference waveform in step S29 (Yes in S29), the timer is cleared (S32), and detection is performed as to whether or not 30 minutes, or the predetermined period of time, have elapsed (S31). When 30 minutes have not yet elapsed (No in S31), processing returns to step S28, where processing is continued.

When cumulative time during which the waveform is determined not to exhibit the feature of the reference waveform is increased by processing pertinent to step S30 and when 30 minutes elapse as a result of updating the time of the timer, which eventually leads to a choice of YES in step S31, processing returns to step S11, where electrocardiogram complex learning is resumed. As above, from the fact that there are many cases in which a waveform is determined not to exhibit the feature of the reference waveform by means of monitoring that uses the reference waveform obtained by special processing, the reference waveform is conceived to be inaccurate. The inaccuracy of the reference waveform can thereby be expected to be amended by resuming electrocardiogram complex learning.

The presently disclosed subject matter is outfitted with determination unit for determining, from arrhythmia determination reference information which is information pertinent to arrhythmia, whether or not an electrocardiogram complex including a first predetermined number of heart beats in a measured electrocardiographic signal is arrhythmia; reference waveform determination unit for determining a reference waveform from the electrocardiogram complex including the first predetermined number of heart beats when the determination unit has determined that the electrocardiogram complex is not arrhythmia; and analysis unit for performing an analysis, by use of the stored reference waveform, as to whether or not the measured electrocardiogram waveform being measured is arrhythmia. It is therefore possible to prevent a problem of a waveform of arrhythmia being determined as a reference waveform.

The presently disclosed subject matter is outfitted with alarm generation unit that generates an alarm representing arrhythmia when the determination unit has determined that the electrocardiogram complex is arrhythmia. Hence, it is possible to expect that arrhythmia can be prevented from being overlooked from the beginning of learning.

What is claimed is:

1. An electrocardiogram analyzer comprising: a measurement section configured to measure an electrocardiographic signal; a determination unit configured to determine, from arrhythmia determination reference information that is pertinent to arrhythmia, whether or not an electrocardiogram complex, which includes a first predetermined number of heart beats, in the thus-measured electrocardiographic signal indicates arrhythmia; a reference waveform determination unit configured to determine a reference waveform from the electrocardiogram complex including the first predetermined number of heart beats when the determination unit has determined that the electrocardiogram complex does not indicate arrhythmia, storing the thus determined reference waveform; an analysis unit configured to perform an analysis as to whether or not an electrocardiogram complex being measured is arrhythmia by use of the stored reference waveform; and a reference waveform manual determination unit configured to manually set the reference waveform, wherein, when the reference waveform manual determination unit is actuated, the reference waveform determination unit performs, without regard to a determination rendered by the determination unit, alternate processing including determining the reference waveform from the electrocardiogram complex including the first predetermined number of heart beats and storing the thus-determined reference waveform.

2. The electrocardiogram analyzer according to claim 1, further comprising a selection unit configured to determine reference waveform candidates from an electrocardiogram complex including a second predetermined number of heart beats, which are essentially identical to each other in terms of a contour, in the measure electrocardiogram signal, wherein the electrocardiogram complex including the first predetermined number of heart beats is selected from the reference waveform candidates.

3. The electrocardiogram analyzer according to claim 1, further comprising an alarm generation unit configured to generate an alarm which represents arrhythmia when the determination unit has determined the electrocardiogram complex as arrhythmia.

4. The electrocardiogram analyzer according to claim 1, wherein when the reference waveform determination unit has performed alternate processing, the analysis unit performs an analysis as to whether or not an electrocardiogram complex which will be subsequently measured exhibit a feature of a reference waveform stored by the reference waveform determination unit; an processing proceeds to a determination which will be made by the determination unit when an electrocardiogram waveform exhibiting the feature of the reference waveform is not detected for a given period of time.

5. An electrocardiogram analyzer, comprising:
a measurement section configured to measure an electrocardiographic signal;
a determination unit configured to determine, from arrhythmia determination reference information that is pertinent to arrhythmia, whether or not an electrocardiogram complex, which includes a first predetermined number of heart beats, in the thus-measured electrocardiographic signal indicates arrhythmia;
a reference waveform determination unit configured to determine a reference waveform from the electrocardiogram complex including the first predetermined number of heart beats when the determination unit has determined that the electrocardiogram complex does not indicate arrhythmia, storing the thus determined reference waveform;
an analysis unit configured to perform an analysis as to whether or not an electrocardiogram complex being measured is arrhythmia by use of the stored reference waveform; and
a reference waveform manual determination unit configured to perform a special processing which includes determining the reference waveform based on the electrocardiogram complex including the first predetermined number of heart beats and then storing the determined reference waveform regardless of a determination by the determination unit.

* * * * *